United States Patent [19]

Tucker

[11] Patent Number: 5,342,324

[45] Date of Patent: Aug. 30, 1994

[54] NEEDLE DEVICE

[75] Inventor: Elton M. Tucker, Medfield, Mass.

[73] Assignee: Device Labs, Inc., Medway, Mass.

[21] Appl. No.: 2,437

[22] Filed: Jan. 8, 1993

[51] Int. Cl.$^5$ ............................................. A61M 5/00
[52] U.S. Cl. .................................. 604/264; 604/117; 604/174; 604/272
[58] Field of Search ............... 604/268, 272, 174, 177, 604/178, 117, 120, 111, 264, 273; 128/DIG. 26

[56] References Cited

U.S. PATENT DOCUMENTS

| | | | |
|---|---|---|---|
| 4,235,234 | 11/1980 | Whitney et al. | 604/117 |
| 4,362,156 | 12/1982 | Feller, Jr. et al. | 604/165 |
| 4,645,495 | 2/1987 | Vaillancourt | 604/177 |
| 4,710,176 | 12/1987 | Quick | 604/177 |
| 4,769,010 | 9/1988 | Fenton et al. | 128/DIG. 26 |
| 4,813,939 | 3/1989 | Marcus | 604/177 |
| 4,880,412 | 11/1989 | Weiss | 604/165 |
| 5,167,639 | 12/1992 | Hollands et al. | 604/180 |

Primary Examiner—John G. Weiss
Attorney, Agent, or Firm—Samuels, Gauthier & Stevens

[57] ABSTRACT

A needle device includes a multi-component housing assembled about a needle having angularly disposed segments. The housing immobilizes the needle during insertion and is adapted for subsequent disassembly and removal from the needle.

13 Claims, 3 Drawing Sheets

NEEDLE DEVICE

BACKGROUND OF THE INVENTION

This invention relates to needle devices of the type incorporating angled needles.

Angled needle devices are employed in various medical procedures, including for example the infusion of fluids into subcutaneous access ports. Typically, as disclosed for example in U.S. Pat. No. 4,710,176 (Quick), such devices include a needle having a penetrating section disposed normally to an inlet section, the latter being surrounded and at least partially encased by a housing which may be grasped and manipulated by medical personnel during insertion of the needle. Ideally, the needle is firmly gripped by and thus immobilized with respect to the housing, thereby facilitating accurate insertion of the penetrating section through the patient's skin and into the subcutaneous access port. Such needle devices may remain in place for protracted periods of time. Thus, after insertion, the housings are usually taped to the patient's skin to immobilize the needle relative to the puncture site. Unfortunately, the resulting bulk of the externally taped housing contributes substantial bulk to the dressing and causes substantial discomfort to the patient. The patient is more likely to be conscious of this discomfort at all times due to the bulk of the dressing and its unsightly appearance.

As disclosed in U.S. Pat. No. 4,235,234 (Whitney et al), attempts have been made at minimizing patient discomfort due to needle mobility by encasing the exterior inlet section of the needle in a thick planar pad designed to lie against the patient's skin. While this arrangement may stabilize the needle after insertion, it presents other problems in that the planar pads obscure the insertion target from the line of sight of medical personnel during insertion, in addition to being difficult to grip and manipulate.

There remains, therefore, a need for an angled needle device which may be reliably, efficiently and accurately manipulated by medical personnel during insertion, and which may thereafter be separated from its insertion aids or grips and may be securely held in place for protracted periods of time without causing undue dressing bulk, unsightly bulges or discomfort to the patient.

SUMMARY OF THE INVENTION

The needle device of the present invention includes an angled needle assembly having a penetrating section disposed normally to an inlet section including a flexible tube leading to a luer connector. The inlet section and an adjacent portion of the penetrating section are encased within and immobilized in relation to a housing which is designed as an insertion aid which may be securely gripped and controllably manipulated by medical personnel during insertion of the needle. The insertion aid housing is made up of multiple releasably coupled components which may be readily separated one from the other to accommodate their removal from the needle assembly following insertion. Once the housing has been removed from the needle, the exterior inlet section of the needle assembly is simply stabilized in place by taping it to the patient's skin. The absence of the insertion aid housing minimizes the resulting surgical dressing bulk and markedly improves patient comfort.

BRIEF DESCRIPTION OF THE DRAWINGS

The invention may be further understood with reference to the accompanying drawings in which.

DETAILED DESCRIPTION OF THE INVENTION

Figure 1:
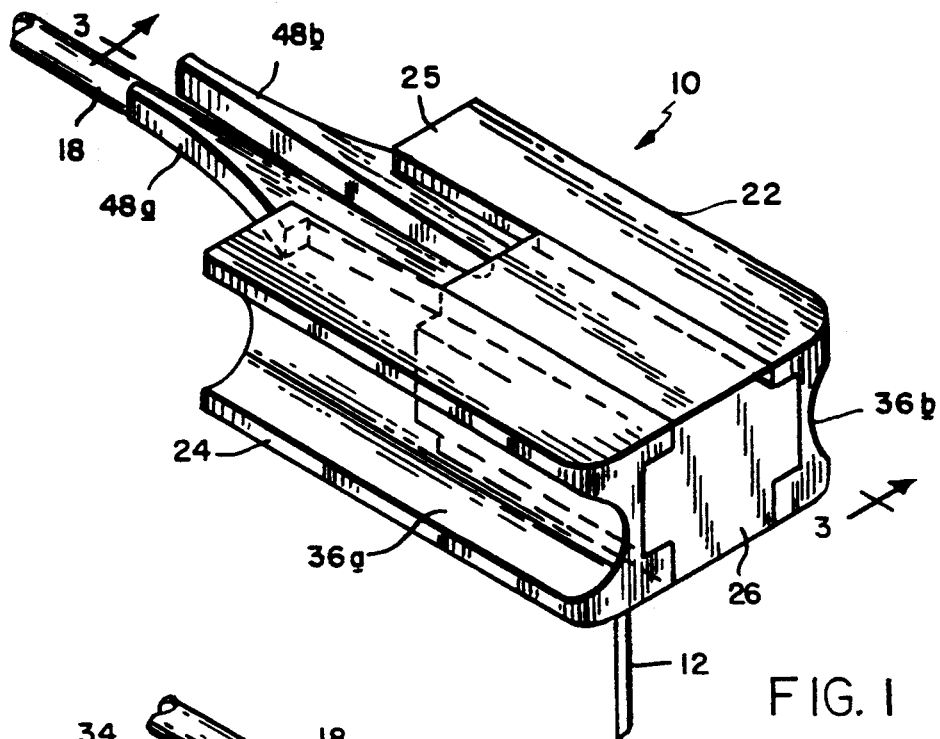
FIG. 1 is an isometric view of a needle device of the present invention.
Figure 2:
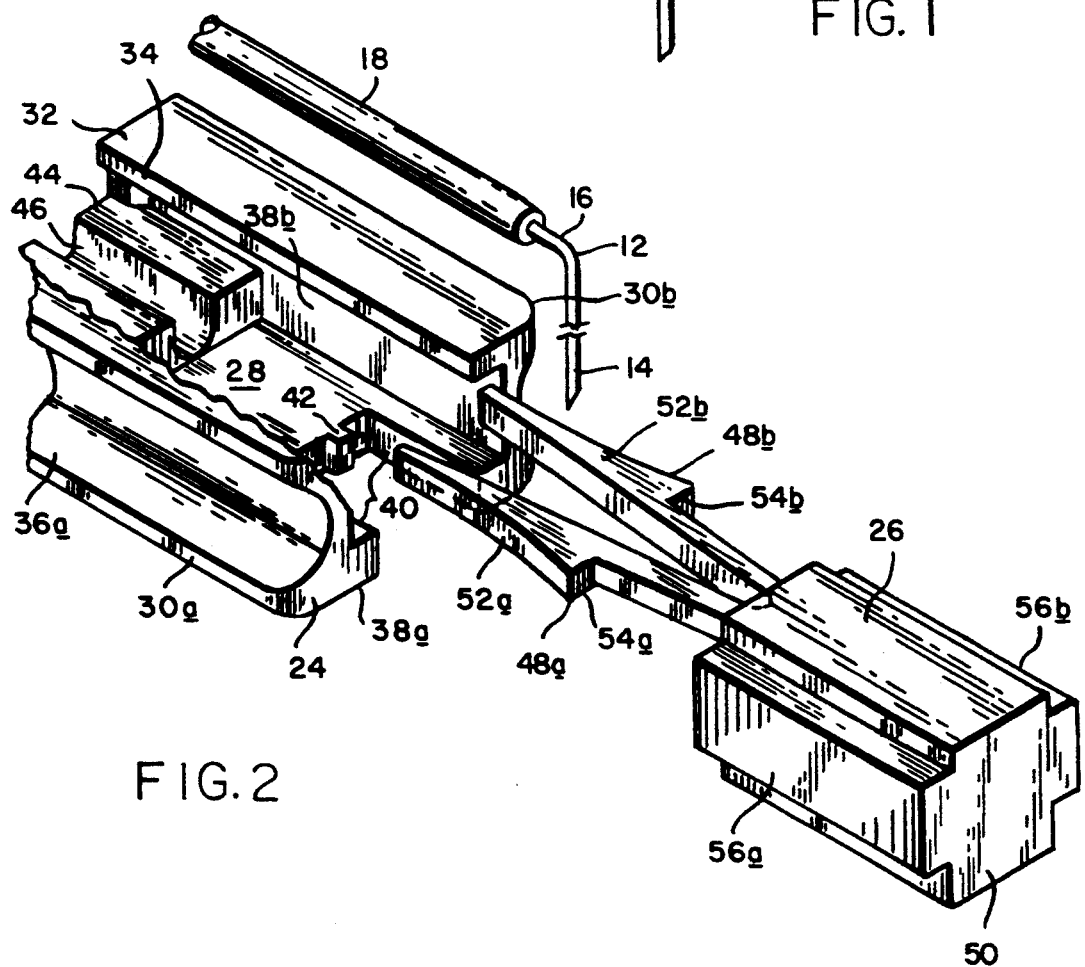
FIG. 2 is an isometric exploded view of the needle device shown in FIG. 1.
Figure 11:
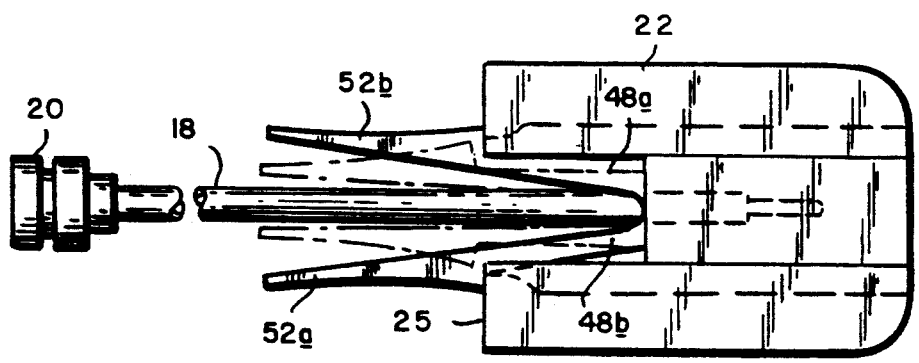
FIG. 11 is a top view of the assembled components shown in FIG. 1 and illustrating the secure and release positions of the tabs.

With reference initially to FIGS. 1 and 2, it will be seen that the needle device 10 of the present invention includes a needle 12 having an insertion section 14 disposed angularly with respect to an inlet section 16, the latter being connected to a flexible tube 18 leading to a luer connector 20 (shown in FIG. 11).

A housing 22 is associated with the needle. The housing includes an outer housing component 24 and an inner housing component 26. The outer housing component 24 is hollow, having a bottom wall 28, upstanding side walls 30a, 30b and a top wall 32 interrupted by a longitudinal slot 34 extending from front to rear. The side walls 30a,30b are externally concave as at 36a,36b respectively to facilitate gripping, and are configured internally to provide longitudinally extending confronting internal guide slots 38a, 38b respectively. The bottom wall 28 is notched as at 40 with a shoulder 42 protruding forwardly from the bottom of the notch 40. A shelf 44 extends across the bottom of the rear of the outer housing 24. The shelf 44 is interrupted by a semi-circular groove 46.

With reference additionally to the remaining figures, it will be seen that the inner housing component 26 is generally L-shaped in cross section with rearwardly diverging wings 48a, 48b, and a depending portion 50. Wings 48a,48b terminate in finger engaging portions 52a, 52b respectively, and are configured to provide locking shoulders 54a,54b respectively. The inner housing component 26 is further provided with side rails 56a, 56b respectively, adapted to be received in and to be guided along the guide slots 38a, 38b respectively of the outer housing 24. As shown in FIGS. 3, 4, 6, and 8 the inner housing component 26 is additionally provided with a longitudinally extending semi-circular groove 58 in its underside leading to a groove 60 in the rear face of depending portion 50.

Figure 3:
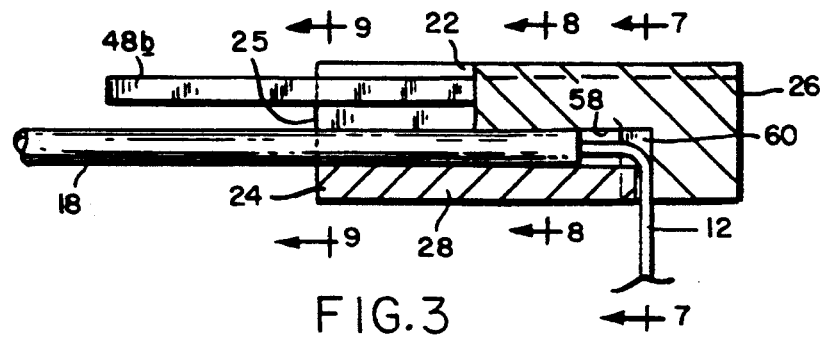
FIG. 3 is a cross-sectional view taken along line 3—of FIG. 1.

The device 10 may be separated such that the inner housing 26, the outer housing 24, and the needle 12 assembly may each be removed from one another as shown in FIG. 2. When locking shoulders 54a, 54b of wings 48a, 48b respectively are mechanically engaged behind the rear wall 25 of the outer housing 24, the inner and outer housing portions 26, 24 are rigidly and releasably assembled together forming the housing 22. As shown in FIG. 3, when the housing 22 is formed, the needle 12 protrudes through the bottom of the device 10.

When assembling the needle device, the needle assembly is first positioned within the outer housing component, with the flexible tube 18 lying in the groove 46 extending across shelf 44, and with the penetrating section 14 of the needle resting against the shoulder 42 at the base of notch 40. The inner housing component 26 is then slid into the outer housing component 24. The side rails 56a, 56b on the inner housing component coact with the internal guide slots 38a, 38b as sliding insertion takes place. As the inner housing component arrives at its fully inserted position, the insertion section 14 of the needle is trapped within the vertical groove 60 in the rear face of depending portion 50, thereby securely and fixedly retaining the insertion portion against the shoulder 42 on the outer housing component 24. At the same time, a portion of the inlet section 16 of the needle encased within the tubing 18 is received within the semicircular groove 58 on the underside of the inner housing component, and is thus fixedly secured against the bottom wall 28 of the outer housing. During insertion of the inner housing component, the rearwardly diverging wings 48a, 48b are in sliding contact with and are thus resiliently urged inwardly by the base surfaces of the guide slots 38a, 38b. When the inner housing component arrives at its fully inserted position, the locking shoulders 54a, 54b on the wings 48a, 48b are located behind the rear wall 25, thereby permitting the wings to resiliently snap outwardly, thus placing the locking shoulders in secure mechanical engagement with the rear wall.

With this arrangement, the needle assembly is securely held against rotation about and/or movement along the axes of both the insertion section 14 and the inlet section 16. The assembled housing is configured and dimensioned to be firmly grasped and efficiently manipulated by medical personnel, with the concave outer surfaces 36a, 36b of the side walls being particularly well suited to receive the finger tips of the user. In alternative embodiments the surfaces could include a relief pattern such as ridges to assist in gripping.

Figure 4:
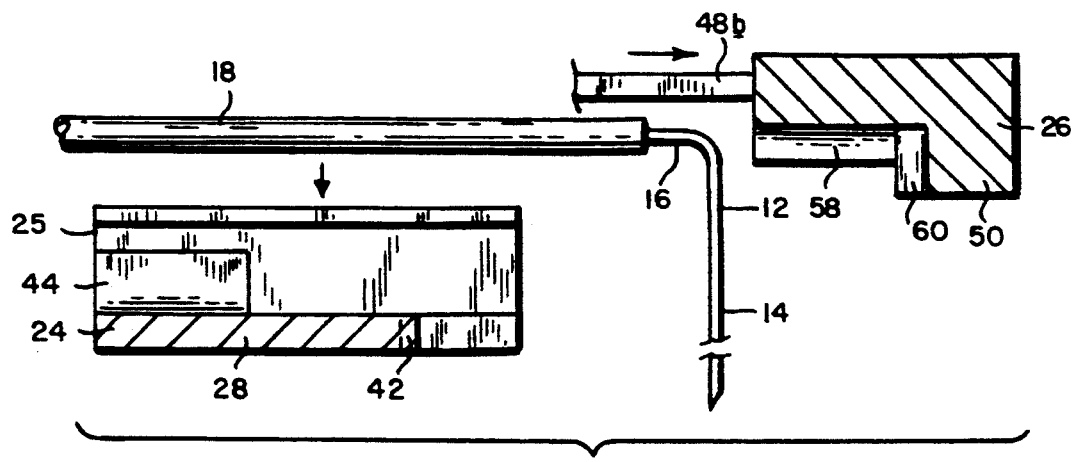
FIG. 4 is an exploded view of the components illustrated FIG. 3.
Figure 5:
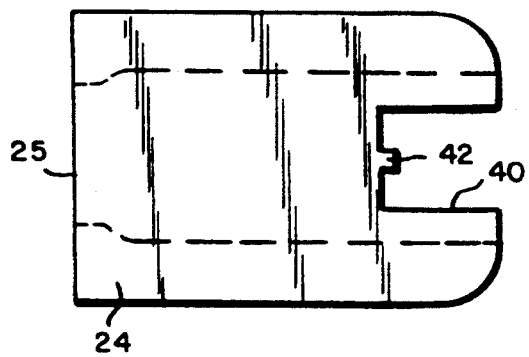
FIG. 5 is a bottom view of the outer housing component.
Figure 6:
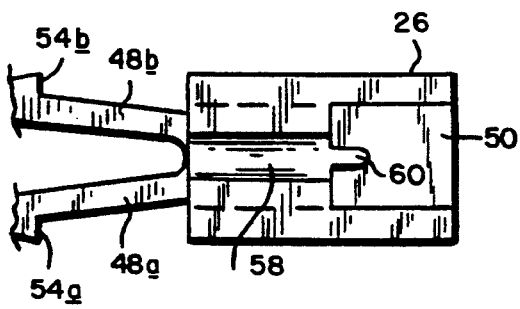
FIG. 6 is a bottom view of the inner housing component.
Figure 7:
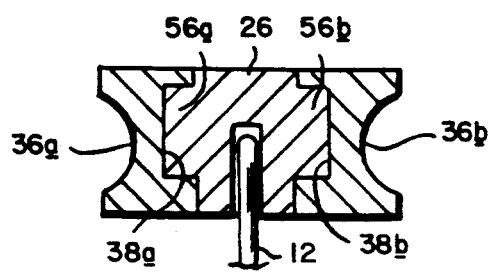
FIGS. 7, 8 and 9 are sectional views taken respectively alone lines 7—7, 8—8 and 9—9 of FIG. 3.
Figure 8:
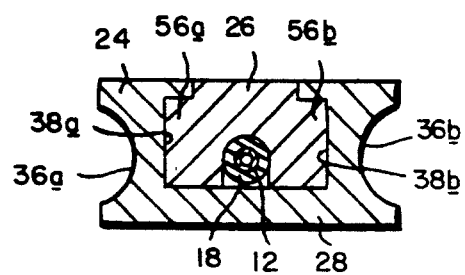
Figure 9:
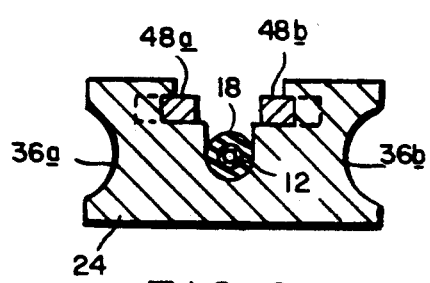
Figure 10:
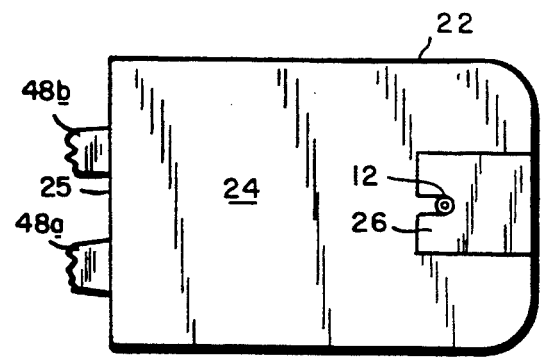
FIG. 10 is a partial bottom view of the assembled components shown in FIG. 1.
Figure 12:
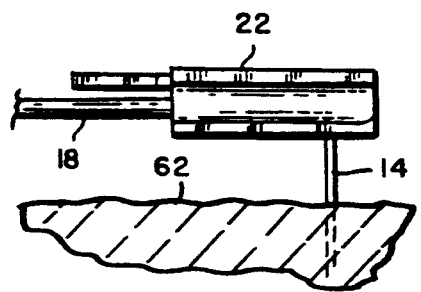
FIG. 12 is a side view of the device shown inserted into a patient.
Figure 13:
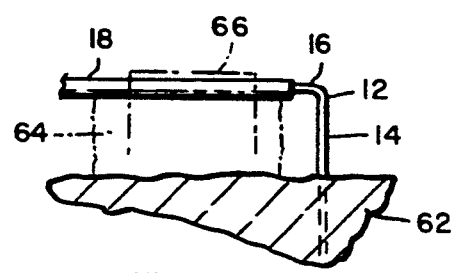
FIG. 13 illustrates the needle following insertion and removed of the housing, with gauze and tape employed to secure the needle in place.

After the insertion section 14 of the needle has been inserted a desired distance into the patient 62, as shown in FIG. 12, the wings 48a, 48b of the inner housing 26 may be resiliently depressed toward each other (such as by finger pressure), as shown in FIG. 11, thereby disengaging the locking shoulders 54a, 54b from the rear wall 25 and freeing the inner housing component 26 for slidable extraction from the outer housing component 24 as shown in FIG. 4. The needle assembly may then be supported by a gauze pad 64 or the like and secured in place by tape 66 as shown in FIG. 13. The tube 18 may include a luer connector 20 at its proximal end, as shown in FIG. 11, for connecting to any conventional fluid supply or receiving apparatus.

Once inserted into a patient 62, the resulting angled needle assembly is freed of the insertion aid housing components and the associated bulk and weight. The invention thus provides for a more open and accessible surface with which health care personnel may work, and a more comfortable needle assembly for patients in need of such a procedure. The device of the invention also substantially eliminates the risk of a patient being adversely affected by the long term presence of a large bulky needle insertion device.

Those skilled in the art will appreciate that numerous modifications and changes may be made to the disclosed embodiments without departing from the scope of the invention.

I claim:

1. A needle device comprising:
   a rigid tubular needle assembly having an insertion section disposed angularly with respect to an inlet section, and
   a housing enclosing said angularly disposed sections with the end of said insertion section protruding exteriorly from said housing, said housing having internal angularly disposed confinement means coacting in engagement with said angularly disposed inlet and insertion sections to immobilize said needle assembly in relation to said housing, said housing being subdivided into multiple releasably coupled components which may be separated one from the other to accommodate removal of said housing from said needle, said confinement means being located at interfaces between said components.

2. A device as claimed in claim 1, wherein said components include cavities for receiving said insertion and inlet sections.

3. A device as claimed in claim 2, wherein said components further include surfaces coacting with said cavities to capture said sections.

4. A device as claimed in claim 1, wherein said angularly disposed sections are disposed at a substantially right angle to one another.

5. A device as claimed in claim 1, wherein said releasably coupled components are releasably coupled along a linear direction defined by said inlet section of said tubular needle assembly.

6. A device as claimed in claim 1, wherein said releasably coupled components include resilient locking members for releasably locking said components together in a snap fit engagement.

7. A device as claimed in claim 1, wherein said housing includes a gripping portion on a side of said housing for facilitating manual control and manipulation of said assembly.

8. A device as claimed in claim 7, wherein said gripping portion includes a concave surface.

9. A device as claimed in claim 1, wherein said device further includes a flexible tube having a distal end connected to an inlet section of said needle.

10. A device as claimed in claim 9, wherein said device further includes a luer connector attached to a proximal end of said flexible tube.

11. A needle device comprising:
    a needle having a proximal end adapted to connect to a flexible tube, a sharpened distal end adapted to be inserted into a subject, and mutually angularly disposed segments between said ends, and
    a housing enclosing said angularly disposed segments with the sharpened distal end of said needle protruding exteriorly from said housing, said housing having stabilizing means for preventing said needle from rotating about either of the axes defined by each of said angularly disposed segments, said housing being subdivided into multiple releasably coupled components which may be separated one from the other to accommodate removal of said housing from said needle without requiring removal of said proximal end from said tubing or removal of said distal end from said subject.

12. A needle device comprising:
a tubular needle assembly having an insertion section disposed angularly with respect to an inlet section, and
a housing enclosing said angularly disposed sections with the end of said insertion section protruding exteriorly from said housing, said housing having internal engagement means for coacting with said sections to immobilize said needle in relation to said housing, said housing being subdivided into multiple releasably coupled components which may be separated one from the other to accommodate removal of said housing from said needle, wherein said releasably coupled components include resilient locking members for releasably locking said components together in a snap fit engagement.

13. A needle device comprising:
a rigid tubular needle assembly having an insertion section disposed angularly with respect to an inlet section, and
a housing enclosing said angularly disposed sections with the end of said insertion section protruding exteriorly from said housing, said housing having immobilizing means for immobilizing said needle thereby preventing said needle from rotating about either of the axes defined by each of said angularly disposed sections, said housing being subdivided into multiple releasably coupled components which may be separated one from the other to accommodate removal of said housing from said needle.

* * * * *